(12) United States Patent
Holmes

(10) Patent No.: US 9,128,036 B2
(45) Date of Patent: Sep. 8, 2015

(54) MULTI-SPECTRAL IMAGING SYSTEM AND METHOD OF SURFACE INSPECTION THEREWITH

(75) Inventor: Nigel John Holmes, Ann Arbor, MI (US)

(73) Assignee: Federal-Mogul Corporation, Southfield, MI (US)

( * ) Notice: Subject to any disclaimer, the term of this patent is extended or adjusted under 35 U.S.C. 154(b) by 955 days.

(21) Appl. No.: 13/052,431

(22) Filed: Mar. 21, 2011

(65) Prior Publication Data

US 2012/0242826 A1 Sep. 27, 2012

(51) Int. Cl.
*A61B 1/06* (2006.01)
*G01N 21/31* (2006.01)
*G01N 21/88* (2006.01)
*G01N 21/95* (2006.01)

(52) U.S. Cl.
CPC .......... *G01N 21/3151* (2013.01); *A61B 1/0638* (2013.01); *G01N 21/8806* (2013.01); *G01N 21/95* (2013.01); *G01N 2021/8845* (2013.01)

(58) Field of Classification Search
CPC ....................................................... A61B 1/06
See application file for complete search history.

(56) References Cited

U.S. PATENT DOCUMENTS

| | | | |
|---|---|---|---|
| 3,817,622 A | 6/1974 | Billman et al. | |
| 5,016,173 A | 5/1991 | Kenet et al. | |
| 5,197,105 A | 3/1993 | Uemura et al. | |
| 5,886,342 A | 3/1999 | Matsui | |
| 6,005,965 A | 12/1999 | Tsuda et al. | |
| 6,291,816 B1 | 9/2001 | Liu | |
| 6,633,375 B1 | 10/2003 | Veith et al. | |
| 6,743,645 B2 | 6/2004 | Kubota et al. | |
| 7,189,984 B2 | 3/2007 | Sawada | |
| 7,289,233 B2 | 10/2007 | Kurokawa et al. | |
| 2003/0068078 A1 | 4/2003 | Swab | |
| 2003/0144650 A1* | 7/2003 | Smith | 606/5 |
| 2003/0147562 A1 | 8/2003 | Damm et al. | |
| 2009/0101822 A1 | 4/2009 | Mitra et al. | |
| 2009/0270678 A1* | 10/2009 | Scott et al. | 600/109 |

FOREIGN PATENT DOCUMENTS

| | | |
|---|---|---|
| DE | 3413027 A1 | 10/1985 |
| EP | 0459489 A2 | 12/1991 |

OTHER PUBLICATIONS

International search report PCT/US2012/027673 mailed on May 21, 2012.

* cited by examiner

*Primary Examiner* — Joseph Ustaris
*Assistant Examiner* — Mikhail Itskovich
(74) *Attorney, Agent, or Firm* — Robert L. Stearns; Dickinson Wright, PLLC

(57) ABSTRACT

A multi-spectral imaging system includes a first light source that emits a first wavelength and a second light source that emits a second wavelength different than the first wavelength. The system further includes a camera having a lens, a beam splitter downstream of the lens and a pair of sensors downstream of the beam splitter. The lens is configured to focus the first and second wavelengths onto separate ones of the sensors, and the beam splitter allows one of the first wavelength or the second wavelength to pass through the beam splitter, and the other of the first wavelength or the second wavelength to be reflected off the beam splitter. One of the pair of sensors is configured to receive the first wavelength to produce a first image and the other of the sensors is configured to receive the second wavelength to produce a second image different from the first image.

11 Claims, 1 Drawing Sheet

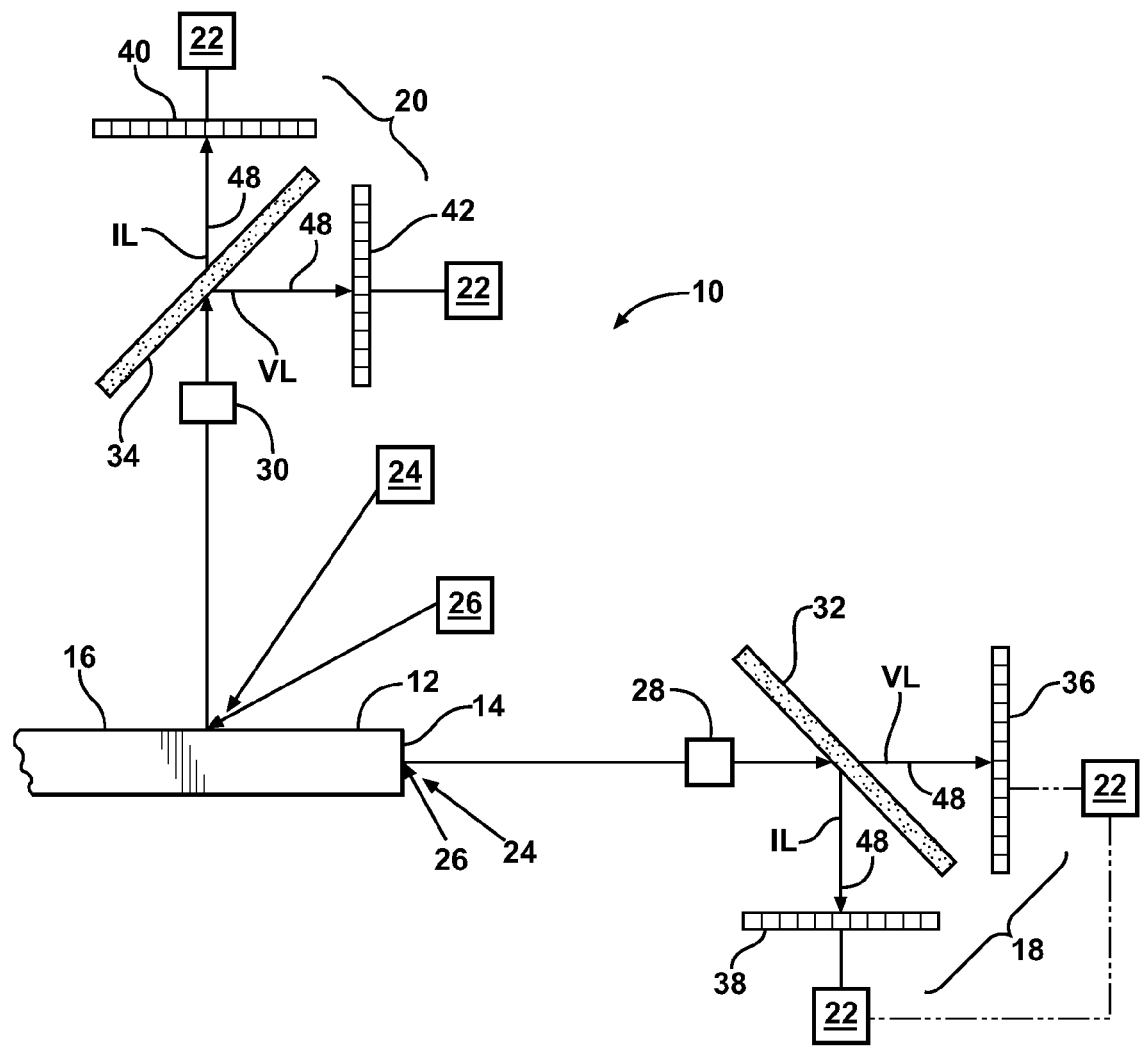

US 9,128,036 B2

MULTI-SPECTRAL IMAGING SYSTEM AND METHOD OF SURFACE INSPECTION THEREWITH

BACKGROUND OF THE INVENTION

1. Technical Field

This invention relates generally to surface inspection systems and methods, and more particularly to inspection systems and methods for inspecting bores.

2. Related Art

Manufactured parts, e.g., vehicle parts, such as seals, gaskets, or pistons, for example, are typically inspected during manufacture to ensure the parts are meeting certain predetermined specifications. Known inspection systems and methods include measurement systems that make physical contact with the parts during manufacture, such as profilometers, for example. These systems obtain data through relative movement between a stylus and the abutting surface of the part. Although this type of inspection system can provide accurate results, it can result in damage to surface being inspected and the inspection results are generally limited to a small portion of the surface being inspected, and further, can be very time consuming.

Other known inspection systems include imaging systems that remain out of contact with the part being inspected. These systems can obtain 2-dimensional data and 3-dimensional data by producing images from different wave lengths of light. In order to produce both 2-D images and 3-D images, at least two separate cameras and two separate light sources are required, with one camera and light source being set-up to produce a first image and the other camera and light source being setup to produce a second image. The separate cameras and light sources can be set-up to obtain an image simultaneously with one another, however, although these systems are capable of generating images of the surface being inspected, they take up valuable manufacturing floor space by nature of having multiple cameras and light sources, and further, the light sources can interfere with one another, thereby producing an less than desirable image quality. As such, in order to avoid light interference, another known inspection system can set-up a single camera with separate light sources to obtain separate images at separate times from one another. However, these systems have the inherent draw back of requiring the surface being inspected to be stationary while the separate images are obtained.

SUMMARY OF THE INVENTION

A multi-spectral imaging system for inspecting a surface to obtain both 2-D and 3-D images includes a first light source for directing first light having a first wavelength onto the surface and a second light source for directing second light having a second wavelength different than the first wavelength onto the surface. The system further includes a camera having a lens, a beam splitter downstream of the lens and a pair of sensors downstream of the beam splitter. The lens is configured to focus the first and second wavelengths onto their respective sensors, and the beam splitter allows one of the first light or the second light to pass through the beam splitter, and the other of the first light or the second light to be reflected off the beam splitter. To obtain a pair of separate focused images through the lens, one of the pair of sensors is configured to receive the first light to produce a first image and the other of the sensors is configured to receive the second light to produce a second image different from the first image.

In accordance with a further aspect of the invention, at least one of the sensors is adjustable along an axis to move closer and further away from the beam splitter.

In accordance with a further aspect of the invention, a method of inspecting a surface of a part is provided. The method includes reflecting a first wavelength of light off the surface and reflecting a second wavelength of light off the surface, wherein the second wavelength is different from the first wavelength. Then, passing the reflected first wavelength of light through a camera lens and passing the reflected second wavelength of light through the same camera lens as the first wavelength of light. Further, reflecting one of the first or second wavelength of light off a beam splitter within the camera and onto a first sensor and refracting the other of the first or second wavelength of light through the beam splitter within the camera and onto a second sensor different from the first sensor. Next, producing a first image of the surface with the first sensor and producing a second image of the surface with the second sensor, wherein the first image is different from the second image.

In accordance with a further aspect of the invention, the method further includes moving at least one of the first or second sensors along an axis toward or away from the beam splitter.

BRIEF DESCRIPTION OF THE DRAWINGS

These and other aspects, features and advantages of a multi-spectral imaging system and method of inspection therewith in accordance with the invention will become more readily appreciated when considered in connection with the following detailed description of presently preferred embodiments and best mode, appended claims and accompanying drawings, in which:

FIG. 1 is a schematic side view of one embodiment of the multi-spectral imaging system of FIG. 1 constructed in accordance with the invention.

DETAILED DESCRIPTION OF PRESENTLY PREFERRED EMBODIMENTS

Referring in more detail to the drawings, FIG. 1 illustrates multi-spectral imaging system (referred to hereafter as "system") generally at 10 configured in accordance with one aspect of the invention. The system 10 generates at least two images of each surface being inspected to increase the quantity of data used to assess, for inspection purposes, whether the surface of the part is within the desired parameters. One of the images obtained is preferably a 2-D image and the other of the images obtained is preferably a 3-D image. The part is represented here, by way of example and without limitation, as a seal 12, having a convex, circular outer peripheral surface 14 and a substantially planar side face surface 16, both surfaces 14, 16 being simultaneously inspected by the system 10. The system 10 includes at least one camera, and is shown here, by way of example and without limitation, as having a pair of cameras 18, 20. One camera 18 is arranged for inspection of the peripheral surface 14 and the other camera 20 is arranged for simultaneous inspection of the side face surface 16. Each camera 18, 20 generates two separate images simultaneously, wherein each image is able to be analyzed, such as by a processor 22, to instantaneously determine whether a particular feature of the surface being inspected is within the desired specifications. Each image of a single surface can be processed separately, or, the processors 22 associated with each camera 18, 20 can be configured in communication with one another to process the images as a single image, such as by overlaying the images with one another, wherein one of the images is mirrored first, to attain an enhanced image of the inspected surface.

The system 10 includes two different light sources, with a first light source 24 emitting a first light of a first wavelength, such as visible light and a second light source 26 emitting a second light having a second wavelength that is different from the first wavelength, such as infrared light. Depending on the location of the surface being inspected, one or more of each of the light sources 24, 26 can be incorporated into the system.

Each camera 18, 20 has a primary lens 28, 30, respectively, and a beam splitter downstream from the respective lens 28, 30, represented here as a first beam splitter 32 in the first camera 18 and a second beam splitter 34 in the second camera 20. Each primary lens 28, 30 is operable and adjustable to focus the first and second wavelengths of light emitted from their respective light sources 24, 26. The beam splitters 32, 34 can be provided as "hot" minors and/or "cold" mirrors, as desired. Hot mirrors allow the visible light to pass and reflect the infrared light, while cold mirrors allow the infrared light to pass and reflect the visible light. For example, the beam splitter 32 is represented as a "hot" minor and the beam splitter 34 is represented as a "cold" minor. It should be recognized that the minors 32, 34 could be arranged differently, wherein both could be "hot" or "cold", if desired.

Each camera 18, 20 has a pair of charge coupled device (CCD) sensors (36, 38), (40, 42), respectively, arranged approximately 90 degrees to one another with the respective beam splitter 32, 34 extending approximately 45 degrees between each of the sensors. The CCD sensors 36, 38 of the first camera 18 are arranged with one sensor, referred to hereafter as the rear sensor 36, being positioned to receive the light transmitted through the beam splitter 32, and with the other sensor, referred to hereafter as the side sensor 38, being positioned to receive the light reflected off the beam splitter 32. The CCD sensors 40, 42 of the second camera 20 are arranged likewise, with one sensor, referred to hereafter as the rear sensor 40, being positioned to receive the light transmitted through the beam splitter 34, and with the other sensor, referred to hereafter as the side sensor 42, being positioned to receive the light reflected off the beam splitter 34.

To produce a pair of focused images from different wavelengths of light through the single lens 28, 30, at least one of the sensors in the respective pairs of sensors (36, 38), (40, 42), at least one of the sensors in each pair is adjustable along an axis 48 toward and away from the respective beam splitter 32, 34. For example, to obtain a focused image from the infrared light emitted from the infrared light source 26, the infrared light needs to be focused after passing through the respective lens 28, 30, as it has a different wavelength than the visible light focused by the lens 28, 30. As such, the sensor receiving the infrared light is configured to be adjustable. Accordingly, where a "hot" minor is incorporated, the respective side sensor 38, 42 would be adjustable along the axis 48, as the infrared light would be reflected off the "hot" minor and onto the side sensor. However, where a "cold" minor is incorporated, the respective rear sensor 36, 40 would be adjustable along the axis 48, as the infrared light would pass through the "cold" mirror and onto the rear sensor.

The system 10 can be readily adapted for use at any point along a manufacturing process, whether at a secondary inspection station, or along a continuous transfer line, for example. With each camera 18, 20 of the system 10 being able to generate two separate images, the amount of manufacturing floor space occupied by the system is minimized. If a single surface is being inspected, the system 10 can include a single camera, whereas if two or more surfaces are being inspected, additional cameras can be incorporated, as desired. As such, as illustrated in FIG. 1, by way of example and without limitation, the camera 18 has a "hot" minor, and thus, the side sensor 38 is adjustable to allow the infrared light (IL) impinging thereon to be focused. The camera 20 has a "cold" mirror, and thus, the rear sensor 40 is adjustable to allow the infrared light (IL) impinging thereon to be focused.

The visible light (VL) and infrared light (IL) emitted from the respective light sources 24, 26 are directed onto the desired area of the seal 12 to be inspected and the light is reflected off the seal 12 and through the respective lens 28, 30. The visible light (VL) and infrared light (IL) pass through the lens 28, 30, and thereafter, the visible and infrared light impinge on the respective beam splitter 32, 34. Depending on the type of beam splitter, whether "hot" or "cold", the visible light (VL) and infrared light (IL) is either passed through (refracted) the beam splitter or reflected therefrom, as discussed above. Regardless, the visible light (VL) is directed to the respective sensor, represented here, by way of example, as being the respective rear and side sensors 36, 42, whereupon a first image is processed, such as at about 5-15 frames per second, thereby providing an overall image of the inspected surface without regard to surface height. The infrared light (IL) is directed to the respective sensor, represented here, by way of example, as being the respective side and rear sensors 38, 40, whereupon a second image is processed, such as at about 150-200 frames per second, thereby providing an image detailing the height of every pixel contained in the 2-D image generated. The first and second images are generated simultaneously, and can be overlaid with one another, if desired.

According to another aspect of the invention, a method of inspecting a surface of a part, such as the seal 12, for example, is provided. The method includes simultaneously impinging the surface of the part to be inspected with a first wavelength of light, e.g. visible light (VL), and a second wavelength of light, e.g. infrared light (IL), from the respective first and second light sources 24, 26. While the light is impinging the surface being inspected, the method further includes moving the part beneath the light, such as by rotating and/or translating the part beneath the light. In the example illustrated, the seal 14 is being rotated with the peripheral surface 14 and the side face surface 16 both being impinged by the visible light (VL) and infrared light (IL). The method further includes reflecting the visible light (VL) and infrared light (IL) off the surface being inspected while the surface is moving, and directing the reflected light through at least one camera lens, represented here, by way of example, as through the respective primary lens 28, 30 of the two separate cameras 18, 20. It should be recognized that a single one of the cameras 18, 20 could be used if only a single surface were being inspected, however, as shown, two separate surfaces are being inspected, and thus, the two cameras 18, 20 are being used. As the light is passing through the respective lens 28, 30, the method includes focusing the visible light (VL) and infrared light (IL) with the lens 28, 30 and then impinging the respective beam splitter 32, 34 with the visible light (VL) and the infrared light (IL). Further, depending on the type of beam splitter employed, either "hot" or "cold", the method includes refracting one of the visible or infrared light through the beam splitter and reflecting the other of the visible or infrared light off the beam splitter. As illustrated in FIG. 1, the example includes passing the visible light (VL) through the first beam splitter 32 and reflecting the infrared light (IL) off the first beam splitter 32, and passing the infrared light (IL) through the second beam splitter 34 and reflecting the visible light (VL) off the second beam splitter 34. Further yet, the method includes impinging the visible light (VL) and the infrared light (IL) onto the respective pair of sensors 36, 38, and 40, 42 within the respective cameras 18, 20 and producing an image with each of the sensors. The image producing step further includes moving at least one of the sensors within each pair of sensors (36, 38), (40, 42) within each camera 18, 20 along the axis 48 to bring the sensor into position to obtain a focused image. In the example illustrated in FIG. 1, the side sensor 38 of the first camera 18 and the rear sensor 40 of the second camera 20 are adjustable or moveable along the axis 48 toward and away from the respective beam splitters 32, 34. The method further includes comparing the images produced with a predetermined specification, such as via the processor 22, to determine whether the inspected surface is within the desired tolerance limits desired. The method can further include overlaying the images obtained from the visible and infrared light by mirroring one of the images prior to the overlaying step.

Accordingly, the system 10 and method of surface inspection provide an ability to obtain separate images of a common part surface simultaneously via a single camera. Additional cameras can be utilized to inspect multiple surfaces if desired, depending on the number and orientation of the surfaces being inspected. Regardless of the number of cameras employed, each camera is able to produce two images, one via receipt of visible light, which generates an overall image of the surface without regard to height dimensions, and the other via receipt of infrared light, which generates a focused image with regard to height dimensions of the surface being inspected. Accordingly, by being able to use a single camera to generate two images, the space required to implement the surface inspection is minimized, and the overall cost associated with the inspection is reduced from those requiring multiple cameras.

Obviously, many modifications and variations of the present invention are possible in light of the above teachings. It is, therefore, to be understood that within the scope of the appended claims, the invention may be practiced otherwise than as specifically described.

What is claimed is:

1. A multi-spectral imaging system for inspecting a surface of a manufactured mechanical component, comprising: comprising:
   a first light source that directs a first beam light having a first wavelength onto the surface;
   a second light source that directs a second beam of light having a second wavelength different from said first wavelength onto the surface;
   a camera having a lens, a beam splitter downstream of the lens and a pair of sensors downstream of said beam splitter, said beam splitter passing the first beam of light through said beam splitter and reflecting the second beam of light off said beam splitter, and first one of said pair of sensors being receiving said first beam of light from said first light source to produce one image and a second one of said pair of sensors receiving said second beam of light from said second light source to produce another image different from said one image;
   a transfer device that moves the component while the first and second beams of light reflect off the surface being inspected; and
   wherein at least one of said sensors moves toward and away from said beam splitter.

2. The multi-spectral imaging system of claim 1 wherein said first light source emits visible light and said light source emits infrared light.

3. The multi-spectral imaging system of claim 2 wherein said sensor receiving said visible light processes a range of 5-15 frames per second and said sensor receiving said infrared light processes a range of 150-200 frames per second.

4. The multi-spectral imaging system of claim 1 further including at least one processor, said pair of sensors being in communication with said processor.

5. The multi-spectral imaging system of claim 3 wherein said processor is configured to overlie said one image and said another image with one another.

6. A method of inspecting a surface of a manufactured mechanical component, comprising:
   reflecting a first wavelength of light off the surface;
   reflecting a second wavelength of light off the surface, the second wavelength being different from the first wavelength;
   moving the part while reflecting the first and second wavelengths of light off the surface being inspected;
   passing the reflected first wavelength of light through a camera lens;
   passing the reflected second wavelength of light through the same camera lens as the first wavelength of light;
   reflecting one of the first or second wavelength of light off a beam splitter within the camera and onto a first sensor;
   passing the other of the first or second wavelength of light through the beam splitter within the camera and onto a second sensor different from the first sensor; and
   moving at least one of the first or second sensors toward and away form the beam splitter to produce a first image of the surface with the first sensor and a second image of the surface with the second sensor, the first image being different from the second image.

7. The method of claim 6 further including emitting one of the first wavelength of light or the second wavelength of light as infrared light and the other of the first wavelength of light or the second wavelength of light as visible light.

8. The method of claim 6 further including configuring at least one processor in communication with the first and second sensors and overlying the first image and the second image with one another with the processor.

9. The method of claim 8 further including mirroring one of the first image or the second image prior to the overlying the first image and the second image with one another.

10. The method of claim 6 further including configuring one of the first sensor or second sensor to process a range 5-15 frames per second and the other of the first sensor or the second sensor to process a range 150-200 frames per second.

11. The method of claim 6 further including reflecting the first wavelength of light and the second wavelength of light off the surface at the same time.

* * * * *

UNITED STATES PATENT AND TRADEMARK OFFICE
CERTIFICATE OF CORRECTION

PATENT NO.           : 9,128,036 B2                                          Page 1 of 1
APPLICATION NO.      : 13/052431
DATED                : September 8, 2015
INVENTOR(S)          : Nigel John Holmes It is certified that error appears in the above-identified patent and that said Letters Patent is hereby corrected as shown below:

Drawings
In Sheet 1 of the Drawings, the label is missing for "FIG. 1".

Specification
In Column 3, line 18, please replace "minors" with --mirrors--.
In Column 3, line 22, please replace "minor" with --mirror--.
In Column 3, line 23, please replace "minor" with --mirror--.
In Column 3, line 24, please replace "minors" with --mirrors--.
In Column 3, line 53, please replace "minor" with --mirror--.
In Column 3, line 55, please replace "minor" with --mirror--.
In Column 3, line 56, please replace "minor" with --mirror--.

Claims
In Column 5, lines 43-44, please replace "comprising: comprising:" with --comprising:--.
In Column 5, line 45, please replace "first beam light" with --first beam of light--.
In Column 5, line 54, please replace "splitter, and first" with --splitter, a first--.
In Column 6, line 7, please replace "said light source" with --said second light source--.
In Column 6, line 16, please replace "processor is configured to" with --processor operates to--.
In Column 6, line 52, please replace "a range 5-15" with --a range of 5-15--.
In Column 6, line 54, please replace "a range 150-200" with --a range of 150-200--.
In Column 6, line 36, please replace "away form" with --away from--.

Signed and Sealed this
Second Day of February, 2016

Michelle K. Lee
*Director of the United States Patent and Trademark Office*